United States Patent [19]

Cook et al.

[11] 4,298,758

[45] Nov. 3, 1981

[54] PROCESS FOR THE PRODUCTION OF PROPYLENE GLYCOL ESTERS FROM CHLOROPROPYL ETHERS

[75] Inventors: Frank T. Cook; Donald G. Prier, both of Baton Rouge, La.

[73] Assignee: The Dow Chemical Company, Midland, Mich.

[21] Appl. No.: 120,438

[22] Filed: Feb. 11, 1980

[51] Int. Cl.$^3$ .................. C07C 67/10; C07C 67/24; C07C 69/16

[52] U.S. Cl. ............................ 560/240; 560/129; 560/263; 560/264; 568/623; 568/680; 568/858

[58] Field of Search ............. 560/240, 236, 264, 263, 560/129; 260/410.6

[56] References Cited

U.S. PATENT DOCUMENTS

| | | | |
|---|---|---|---|
| 2,283,764 | 5/1942 | Rosenbach | 560/264 |
| 2,847,456 | 8/1958 | Hurd | 560/240 |
| 2,871,248 | 2/1959 | Kirkland et al. | 260/410.6 |
| 2,910,490 | 10/1959 | Malkemus | 260/410.6 |
| 3,061,649 | 10/1962 | Erickson et al. | 560/240 |
| 4,087,453 | 5/1978 | Sherrod et al. | 560/240 |

FOREIGN PATENT DOCUMENTS

| | | | |
|---|---|---|---|
| 913865 | 12/1962 | United Kingdom | 560/240 |
| 180583 | 9/1966 | U.S.S.R. | 560/240 |

OTHER PUBLICATIONS

Groggings, Unit Processes in Organic Syntheses, pp. 718–719.

*Primary Examiner*—Vivian Garner
*Attorney, Agent, or Firm*—A. C. Ancona

[57] ABSTRACT

Propylene glycol and dipropylene glycol diesters are prepared by reacting dichloropropyl ethers with a carboxylic acid salt, e.g., sodium acetate, and the corresponding carboxlyic acid, e.g., acetic acid. The by-product sodium chloride is insoluble in the acetic acid and easily separated from the reaction mixture. The diesters can be hydrolyzed to their respective glycols.

3 Claims, No Drawings

PROCESS FOR THE PRODUCTION OF PROPYLENE GLYCOL ESTERS FROM CHLOROPROPYL ETHERS

BACKGROUND OF THE INVENTION

Dichloroisopropyl ether (DCIPE) is a by-product in the chlorohydrin process for making propylene oxide and is normally burned to recover the chlorine and heat values since there is no apparent use for it. No easy conversion to any other useful product is known. Thus, if a process could be developed to produce an already marketable product, the value of this by-product would be enhanced.

SUMMARY OF THE INVENTION

It has now been discovered that a simultaneous hydrolysis of the chlorines and an esterification can be accomplished by reacting the DCIPE with a carboxylic acid and an alkali metal salt thereof. Some cleaving of the ether occurs and the product obtained is a mixture of the diesters of propylene glycol and of dipropylene glycol. The alkali metal chloride is insoluble in the reaction mixture and can be removed by filtration or centrifugation.

The reaction is carried out at a temperature of about 200° C. and autogenous pressure, usually about 250 psig, for a time sufficient to completely convert the DCIPE. The ratio of the carboxylic acid salt to the DCIPE is equal to or greater than 2.

The product is predominantly a mixture of dipropylene glycol and propylene glycol diacetates at a ratio of about 2/1.

DETAILED DESCRIPTION OF THE INVENTION

The reaction of DCIPE, also named 1,1'-oxybis (1-methyl-2-chloroethane), with sodium acetate (NaOAc) and acetic acid (HOAC) is conducted employing about 2-5 moles of NaOAc per mole of DCIPE under a temperature of 125°-300° C. and a pressure of from about atmospheric up to about 1000 pounds per square inch guage for a period of time sufficient to convert all of the DCIPE, usually eleven hours. Water may be present in the reaction mixture, but the rate of reaction is slowed thereby. No more than about 30 percent water, based on the ether, should be present. By-product formation becomes excessive beyond this amount, and in addition the reaction takes an impractical amount of time. The principal by-product is 2-(1-methyl-2-chloroethoxy)-1-propyl acetate ester.

The reaction time is shorter as the temperature is increased. Generally a time in the range of from about 2 to about 12 hours is employed depending upon the temperature employed.

The amount of acetic acid used is not critical, but generally is present in a mole ratio of from about 5 to about 50 moles per mole of acetate salt used. A preferred ratio is from about 15 to about 30. If the mole ratio of NaOAc/DCIPE is below 2/1 decomposition of the DCIPE occurs at the reaction temperatures.

EXAMPLE 1

In a one liter pressure container (Paar bomb) a mixture of 0.25 mol of DCIPE, 0.5 mol NaOAc and 20 mol (500 ml) HOAc was heated to 200° C. under autogenous pressure with stirring for three hours. The container was then cooled and the reaction mixture was removed from the container and filtered to separate the NaCl. The filtrate was diluted with water and extracted with carbon tetrachloride. The extractant $CCl_4$ was then distilled from the product and analysis showed no DCIPE present, i.e. conversion was 100%. The product contained 30% by weight propylene glycol diacetate and 60% by weight dipropylene glycol diacetate, the remainder consisting primarily of the monoacetate of propylene glycol and 1-chloro-1'acetoxy bis (2,2'oxypropane).

The esters may be hydrolyzed and their respective glycols recovered by methods known to the art.

We claim:

1. The preparation of propylene glycol esters from dichloroisopropyl ether by reacting said ether with a lower carboxylic acid and an alkali metal salt of said acid at elevated temperature in the range of about 125° to 300° C. and pressure in the range of from about atmospheric up to about 1000 pounds per square inch guage for a time sufficient to convert substantially all of said chloroether to form a mixture of propylene glycol and dipropylene glycol diesters wherein the mol ratio of the salt to the chloroether is at least about 2 to 1.

2. The process of claim 1 wherein the lower carboxylic acid is acetic acid.

3. The process of claim 2 wherein the alkali metal salt is the salt of sodium.

* * * * *